United States Patent
Turner

(10) Patent No.: US 10,632,062 B2
(45) Date of Patent: Apr. 28, 2020

(54) HAIR CARE COMPOSITION

(71) Applicant: Joyce Turner, Sumerville, SC (US)

(72) Inventor: Joyce Turner, Sumerville, SC (US)

(*) Notice: Subject to any disclaimer, the term of this patent is extended or adjusted under 35 U.S.C. 154(b) by 0 days.

(21) Appl. No.: 15/950,513

(22) Filed: Apr. 11, 2018

(65) Prior Publication Data
US 2019/0314267 A1    Oct. 17, 2019

(51) Int. Cl.
*A61K 8/92* (2006.01)
*A61K 8/34* (2006.01)
*A61Q 5/06* (2006.01)

(52) U.S. Cl.
CPC .............. *A61K 8/922* (2013.01); *A61K 8/34* (2013.01); *A61K 8/342* (2013.01); *A61K 8/345* (2013.01); *A61Q 5/06* (2013.01)

(58) Field of Classification Search
None
See application file for complete search history.

(56) References Cited

U.S. PATENT DOCUMENTS

| | | |
|---|---|---|
| D641,635 S | 7/2011 | Wang-Treadway |
| 8,449,895 B1 | 5/2013 | Koiteh |
| 8,668,943 B2 | 3/2014 | Hall |
| 8,765,157 B2 | 7/2014 | Blomberg |
| 8,815,225 B2 | 8/2014 | Beumer |
| 2009/0056734 A1 | 3/2009 | Bacon |
| 2012/0204894 A1 | 8/2012 | Odoms |
| 2015/0374613 A1* | 12/2015 | Kirakosyan ............ A61K 8/922 424/727 |

FOREIGN PATENT DOCUMENTS

WO    WO2007098888    9/2007

OTHER PUBLICATIONS https://web.archive.org/web/20120525220149/https://www.walgreens.com/store/c/cantu-shea-butter-coconut-curling-cream/ID=prod6084056-product, on-line publication: 2012, pp. 1-2 (Year: 2012).*
CurlyNikki (obtained from on-line website: https://web.archive.org/web/20150614020659/http://www.curlynikki.com:80/2014/08/mineral-oil-for-reducing-frizz-and.html, on-line publication: Jun. 14, 2015, pp. 1-6 (Year: 2015).*

* cited by examiner

*Primary Examiner* — Kyung S Chang

(57) ABSTRACT

A hair care composition includes a mixture including olive oil, a hair curl controlling cream, unrefined *Vitellaria paradoxa* (shea) butter and baby oil cream.

1 Claim, No Drawings

HAIR CARE COMPOSITION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to hair care products and more particularly pertains to a new hair care product for healing dry and damaged hair.

BRIEF SUMMARY OF THE INVENTION

An embodiment of the disclosure meets the needs presented above by generally comprising a mixture including olive oil, a hair curl controlling cream, unrefined *Vitellaria paradoxa* (shea) butter and baby oil cream.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

Not Applicable

DETAILED DESCRIPTION OF THE INVENTION

A new hair care product embodying the principles and concepts of an embodiment of the disclosure will be described.

The hair care composition described herein is utilized by a person to provide moisture and shine to their hair without building up I the hair. Generally, the hair care composition includes a mixture of olive oil, a hair curl controlling cream, *Vitellaria paradoxa* (shea) butter and baby oil cream.

More specifically, the composition comprises a mixture of:

1) 55% to 65% by weight of a hair curl controlling cream, wherein the hair curl controlling cream includes water, canola oil, glycerin, cetearyl alcohol, ceteareth-20, *Vitellaria paradoxa* butter, *Aloe barbadensis* leaf juice and *Cocos nucifera* oil (Coconut);
2) 25% to 35% by weight unrefined *Vitellaria paradoxa* butter;
3) 7% to 11% by weight baby oil cream, said baby oil including water and mineral; and
4) 1% to 3% olive oil.

The above ingredients are blended together to achieve a homogenous mixture that results in a cream which has enough viscosity that it cannot be poured out of a container but which retains a creamy consistency.

Hair curl controlling creams are ubiquitous in the hair care arts and typically comprise a combination of water, oils and fragrances. Once such suitable hair curl controlling cream is *Cantu* Coconut Curling Cream available from AB Brands, 5501 LBJ Freeway, Suite 900, Dallas, Tex. This particular hair curl controlling cream includes water, canola oil, glycerin, cetearyl alcohol, ceteareth-20, fragrance, *Vitellaria paradoxa* butter (Shea), ceteth-20, glycol stearate, petrolatum, *Aloe barbadensis* Leaf Juice (*Aloe Vera*), *Cocos nucifera* oil (Coconut), *Simmondsia chinensis* seed oil (Jojoba), *Glycine soja* Oil (Soybean), *Persea gratissima* oil (Avocado), *Prunus Amygdalus* dulcis oil (Sweet Almond), *Mangifera indica* (Mango) seed butter, *Olea Europaea* fruit oil (Olive), *Macadamia ternifolia* seed oil (Macadamia), *Melia azadirachta* seed oil (Neem), *Daucus Carota sativa* seed oil (Carrot), *Argania spinosa* kernel oil (Argan), silk amino acids, *Lonicera japonica* flower extract (Honeysuckle), *Laminara cloustoni* extract (Sea Kelp), *Salvia officinalis* (Sage) leaf extract, *Vitis vinifera* seed extract (Grape), *Urtica dioica* extract (Nettle), PEG-75, polyquaternium-10, phenoxyethanol, ethylhexylglycerin.

The 25% to 35% *Vitellaria paradoxa* butter is 100% unrefined shea butter and may be purchased from any one of numerous suppliers. One such supplier is MJ Cosmetics, 11 Elkhorn Court, North Lakes, Queensland Australia.

The baby oil cream is typically a mineral oil which is mixed with water and blended with stabilizers to achieve a creamy consistency which is more viscous than regular baby oil. Such creams are widely available though one suitable brand is Angel of Mine creamy baby oil available from Greenbrier International Inc., 500 Volvo Parkway, Chesapeake, Va. 23320.

The olive oil would generally comprise virgin olive oil. Such is ubiquitously found in grocery stores and no particular brand is preferred.

In use, the composition a light weight cream that is applied to a person's hair for deep conditioning or as a daily moisturizer. The composition corrects dryness in a person's hair and will add shine to the hair.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A hair care composition consisting of:

1% to 3% by weight of olive oil;

55% to 65% by weight of a hair curl controlling cream, said hair curl controlling cream including water, canola oil, glycerin, cetearyl alcohol, ceteareth-20, *Vitellaria paradoxa* butter, *Aloe barbadensis* leaf juice and *Cocos nucifera* oil (Coconut);

25% to 35% by weight unrefined *Vitellaria paradoxa* butter; and

7% to 11% by weight baby oil cream, said baby oil including water and mineral oil.

* * * * *